US012187776B2

(12) United States Patent
Gilham et al.

(10) Patent No.: US 12,187,776 B2
(45) Date of Patent: Jan. 7, 2025

(54) POOLING SIGNALING AND COSTIMULATORY DOMAINS IN B7H6 CHIMERIC ANTIGEN RECEPTOR

(71) Applicant: CELYAD S.A, Mont-Saint-Guibert (BE)

(72) Inventors: David Gilham, Mont-Saint-Guibert (BE); Jennifer Bolsée, Mont-Saint-Guibert (BE); Lorraine Springuel, Mont-Saint-Guibert (BE)

(73) Assignee: CELYAD S.A., Mont-Saint-Guibert (BE)

( * ) Notice: Subject to any disclaimer, the term of this patent is extended or adjusted under 35 U.S.C. 154(b) by 526 days.

(21) Appl. No.: 16/772,183

(22) PCT Filed: Dec. 14, 2018

(86) PCT No.: PCT/EP2018/085089
§ 371 (c)(1),
(2) Date: Jun. 12, 2020

(87) PCT Pub. No.: WO2019/115818
PCT Pub. Date: Jun. 20, 2019

(65) Prior Publication Data

US 2021/0070831 A1 Mar. 11, 2021

(30) Foreign Application Priority Data

Dec. 14, 2017 (EP) .................................... 17207309

(51) Int. Cl.

| | |
|---|---|
| ***C07K 14/725*** | (2006.01) |
| ***A61K 39/00*** | (2006.01) |
| ***A61P 35/00*** | (2006.01) |
| ***C07K 14/705*** | (2006.01) |
| ***C07K 16/28*** | (2006.01) |
| ***C12N 5/0783*** | (2010.01) |

(52) U.S. Cl.
CPC ...... *C07K 14/7051* (2013.01); *A61K 39/4611* (2023.05); *A61K 39/4631* (2023.05); *A61K 39/464429* (2023.05); *A61P 35/00* (2018.01); *C07K 14/705* (2013.01); *C07K 16/2827* (2013.01); *C12N 5/0636* (2013.01); *C07K 2317/622* (2013.01); *C07K 2319/02* (2013.01); *C07K 2319/03* (2013.01)

(58) Field of Classification Search
CPC ............ C07K 14/7051; C07K 16/2827; C07K 2319/02; C07K 2319/03; A61K 35/17; C12N 5/0636
See application file for complete search history.

(56) References Cited

U.S. PATENT DOCUMENTS

| | | | |
|---|---|---|---|
| 2012/0282256 A1 | 11/2012 | Campana et al. |
| 2017/0081411 A1 | 3/2017 | Boris et al. |

FOREIGN PATENT DOCUMENTS

| | | |
|---|---|---|
| WO | 2006036445 | 4/2006 |
| WO | 2014127261 | 8/2014 |
| WO | 2014145252 | 9/2014 |
| WO | 2016044605 | 3/2016 |

*Primary Examiner* — Elly-Gerald Stoica
(74) *Attorney, Agent, or Firm* — Robin L. Teskin; Baker, Donelson, Bearman, Caldwell & Berkowitz PC

(57) ABSTRACT

The present application relates to the field of immunotherapy, more particularly to the field of chimeric antigen receptors (CARs). Currently, second and third generation CAR designs are quite rigid in that they combine fixed costimulatory domains in cis on the same intracellular protein domain. Trans signaling is not equivalent as costimulatory receptors have different expression levels or stoichiometry. Here, a 'mix and match' approach is proposed where different signaling and costimulatory domains are present on separate chains within the same CAR complex, allowing increased flexibility and control of the nature and strength of the CAR-generated signal. Also proposed are polynucleotides, vectors encoding the transmembrane polypeptide chains and cells expressing such CARs. These cells are particularly suitable for use in immunotherapy, and strategies to treat diseases such as cancer using these cells are also provided.

12 Claims, 5 Drawing Sheets

A

B

POOLING SIGNALING AND COSTIMULATORY DOMAINS IN B7H6 CHIMERIC ANTIGEN RECEPTOR

CROSS-REFERENCE TO RELATED APPLICATIONS

This application is a U.S. National Phase Application of Int'l Appl. No. PCT/EP2018/085089, filed Dec. 14, 2018, which claims priority to Int'l Appl. No. EP 17207309.0, filed Dec. 14, 2017, each of which is incorporated herein by reference.

FIELD OF THE INVENTION

The present application relates to the field of immunotherapy, more particularly to the field of chimeric antigen receptors (CARs). Currently, second and third generation CAR designs are quite rigid in that they combine fixed costimulatory domains in cis on the same intracellular protein domain. Trans signaling is not equivalent as costimulatory receptors have different expression levels or stoichiometry. Here, a 'mix and match' approach is proposed where different signaling and costimulatory domains are present on separate chains within the same CAR complex, allowing increased flexibility and control of the nature and strength of the CAR-generated signal. Also proposed are polynucleotides, vectors encoding the transmembrane polypeptide chains and cells expressing such CARs. These cells are particularly suitable for use in immunotherapy, and strategies to treat diseases such as cancer using these cells are also provided.

BACKGROUND

Improvements in our understanding of the immune system have led to the development of many immune focused therapies that are now delivering objective clinical responses in patients with advanced cancer. One of these approaches is the Chimeric Antigen Receptor (CAR) T cell where patients' T cells are gene-modified to express a tumor targeting CAR and then returned to the patient in large numbers (1). This adoptive cell therapy has achieved a level of validation through objective clinical responses in patients with hematological malignancies and is being further explored for the therapy of broader cancer indications (2-7). The CAR concept is also moving beyond T cells with CARs being explored in a range of cell types including Natural Killer cells (8).

CARs are modular protein receptors that consist of a target binding domain linked to structural domains that generally include an extracellular spacer domain and a transmembrane region fused to intracellular signaling domains. Upon ligand binding, downstream signaling initiated from the CAR activates the effector function of the T cell thereby driving direct tumor cell killing and immune-recruiting cytokine production. However, T cells require two signals to become fully activated. A first signal, which is antigen-specific, is provided through the T cell receptor (or TCR) which interacts with peptide-MHC molecules on the membrane of antigen presenting cells (APC). A second signal, the co-stimulatory signal, is antigen nonspecific and is provided by the interaction between co-stimulatory molecules expressed on the membrane of APC and the T cell.

To incorporate this feature in CARs, the modular structure has been extended from first-generation CARs with only a CD3ζ signaling domain to second and third generation CARs that link the signaling endodomains of e.g. CD28, 4-1BB, or OX40 to CD3ζ in an attempt to mimic costimulation (the second signal) that is provided during TCR recognition by antigen presenting cells, and required for full physiologic T cell activation. The approach of providing one or more co-stimulatory signals in "cis" in second and third generation CARs augments cytokine production and proliferation of CAR-T cells in vitro, and second generation CD19-specific CARs carrying CD28 or 4-1BB signaling moieties have demonstrated potent in vivo antitumor activity in pre-clinical models and clinical trials for B cell malignancies.

However, these designs are artificial by nature, and the fact that the costimulatory domain(s) is/are present in a fixed amount and orientation reduces the flexibility of the natural system. It has been reported that the use of different costimulatory domains yield to different kinetics and persistence in vivo, and even the proximity of the costimulatory domain to the membrane seems to play a role (Zhao et al., Cancer Cell, 2015, p 415-428). Providing costimulation in trans through an additional ligand/receptor interaction (as happens in a natural TCR) will result in spatial and temporal differences in the recruitment, kinetics and regulation of costimulation. For instance, the constitutive expression of CD80 on the T cell surface is not expected to be equivalent to the inclusion of the CD28 signaling domain within the CAR due to CTLA4 inhibition and receptor downregulation (Condomines et al., PloS One 2015); while in other instances trans signaling outperforms second generation CAR design (Curran et al., Mol Ther. 2015). To further complicate matters, the standard CAR design is a dimeric structure, whereas the natural conformation of e.g. activated 4-1BB is trimeric (van der Stegen et al., 2015), a structural difference that could affect downstream signaling efficacy (Park et al., 1999).

To improve CAR signaling, and in particular to improve the flexibility of the system, it would be advantageous to have a modulatory design, where it is possible to incorporate or interchange more than one costimulatory domains, in a stoichiometrically controlled way. This would allow better control of the CAR signal, and selecting the best CAR signal according to the circumstances. It could even be envisaged that negative costimulatory domains can be incorporated to control the CAR-induced signal.

SUMMARY

The current invention is based on the finding that, whereas CARs typically function as a dimeric structure, this need not be the case. For instance, CARs based on the NKG2D receptor (such as those described in WO2006/036445) with a NKG2D transmembrane domain, rely on the signal of endogenous DAP10 molecules for full activation. The association of NKG2D with DAP10 is based on transmembrane interactions, primarily based on opposite charges and further stabilized by non-charged interactions. This association primarily based on opposite charges of transmembrane domains is well-documented in immune cells for e.g. the hexameric complex of NKG2D with DAP10 or DAP12 and for the octomeric TCR complex.

The present inventors showed that such signals can be modified: the endogenous DAP10 costimulatory domains can be replaced or supplemented with other costimulatory domains, as long as the transmembrane interaction remains intact (in this example: based on the transmembrane NKG2D-DAP10 or NKG2D-DAP12 interaction). This offers a number of advantages which combine the best of cis and trans CAR signaling: by using a CAR complex that adds accessory chains (through transmembrane-mediated interactions) to the antigen-binding CAR chain, signaling and costimulatory signals can be incorporated in different chains in the same complex, providing a flexible 'mix and match' approach to provide the optimal signal according to the circumstances.

Accordingly, it is an object of the invention to provide modular CAR complexes where a CAR transmembrane protein chain with an antigen-binding domain (that determines the specificity of the CAR) is provided together with an accessory transmembrane protein chain that has a transmembrane region that associates with the transmembrane region of the CAR protein chain, and wherein the CAR protein chain and the accessory protein chain each have a signaling domain or a costimulatory domain, so that the complex containing both protein chains has at least one of each.

Thus, according to a first aspect, combinations of at least two isolated nucleic acid molecules are provided, wherein

- at least one nucleic acid molecule encodes a chimeric antigen receptor (CAR), wherein the CAR comprises an antigen binding domain, a first transmembrane domain, and a signaling domain or costimulatory domain;
- at least a second nucleic acid molecule encodes an accessory protein comprising a second transmembrane domain and a signaling domain or costimulatory domain;
- wherein the first transmembrane domain of the CAR molecule associates with the second transmembrane domain of the accessory protein; and
- wherein the combination comprises both a signaling domain and a costimulatory domain, where one is encoded in the first and one in the second nucleic acid molecule.

According to specific embodiments, combinations of two isolated nucleic acid molecules are provided, wherein

- the first nucleic acid molecule encodes a chimeric antigen receptor (CAR), wherein the CAR comprises an antigen binding domain, a first transmembrane domain, and a signaling domain or costimulatory domain;
- the second nucleic acid molecule encodes an accessory protein comprising a second transmembrane domain and a signaling domain or costimulatory domain;
- wherein the first transmembrane domain of the CAR associates with the second transmembrane domain of the accessory protein; and wherein the combination comprises both a signaling domain and a costimulatory domain, where one is encoded in the first and one in the second nucleic acid molecule.

According to particular embodiments, the signaling domain is selected from the group consisting of a CD3 zeta chain, a Fc epsilon RI gamma chain and a CD3 epsilon chain. According to further particular embodiments, the signaling domain is a CD3 zeta chain.

According to particular embodiments, the costimulatory domain is selected from the group consisting of CD28, 4-1BB, OX40, ICOS, DAP10, DAP12, CD27, and CD2.

According to specific embodiments, the second nucleic acid molecule encodes a chimeric protein.

According to specific embodiments, the antigen binding domain is an scFv, the ligand binding domain of a receptor, an antibody or a VHH.

According to particular embodiments the first and second transmembrane domains have an opposite charge (i.e., one TM domain has a net positive charge, and the other TM domain has a net negative charge) and the association is at least in part through ionic interactions. According to further particular embodiments, the positively charged transmembrane domain is a transmembrane domain from a natural killer (NK) receptor. Particularly, the transmembrane domain is from a NK receptor selected from type I transmembrane receptors such as NKp30, NKp44 or NKp46, or from type II transmembrane receptors such as the NKG2 family members (NKG2A, NKG2B, NKG2C, NKG2D, NKG2E, NKG2F, and NKG2H). According to a specific embodiments, the transmembrane domain is from a type I transmembrane NK receptor. According to specific embodiments, the transmembrane domain is a NK receptor based transmembrane domain selected from NKp44 and NKG2D transmembrane domains.

According to alternative embodiments, the transmembrane domain is an artificial transmembrane domain. Particularly envisaged are polyleucine transmembrane domains. As leucine residues are not charged, these will be polyleucine transmembrane domains with an insertion of one, two or three charged residues. The charged residues will either be positively or negatively charged (but will typically be of the same charge if more than one is used, as otherwise the charge will be neutralized). Particularly envisaged positively charged residues are arginine and lysine. Particularly envisaged negatively charged residues are glutamic acid and aspartic acid. Particularly envisaged is a positively charged polyleucine transmembrane domain with an arginine at position 11 or 12 (as compared to the NKG2D reference TM sequence).

According to particular embodiments, the negatively charged transmembrane domain is selected from a DAP10 and a DAP12 transmembrane domain. According to alternative embodiments, the negatively charged transmembrane domain is an artificial transmembrane domain. Particularly envisaged are polyleucine transmembrane domains with a negatively charged residue, as explained above.

According to further particular embodiments, the positively charged transmembrane domain is a transmembrane domain from a natural killer (NK) receptor and the negatively charged transmembrane domain is selected from a DAP10 and a DAP12 transmembrane domain. According to yet further particular embodiments, the NK receptor based transmembrane domain is present in the CAR chain.

According to a further aspect, nucleic acid molecules are provided encoding a chimeric antigen receptor, wherein the CAR comprises an antigen binding domain, a transmembrane domain, and a signaling domain or costimulatory domain; and wherein the transmembrane domain is a NK receptor transmembrane domain and the antigen binding domain is not from the same NK receptor. For instance, a NKG2D transmembrane domain and an antigen binding domain that is not the NKG2D receptor; or a NKp44 transmembrane domain and an antigen binding domain that is not the NKp44 receptor. According to alternative embodiments, nucleic acid molecules are provided encoding a chimeric antigen receptor, wherein the CAR comprises an antigen binding domain, a transmembrane domain that comprises a polyleucine sequence with one to three charged residues and a signaling domain or costimulatory domain. The charged residues will either be positively or negatively charged (but will typically be of the same charge if more than one is used, as otherwise the charge will be neutralized). Particularly envisaged positively charged residues are arginine and lysine. Particularly envisaged negatively charged residues are glutamic acid and aspartic acid. Particularly envisaged is a positively charged polyleucine transmembrane domain with an arginine at position 11 or 12 (as compared to the NKG2D reference TM sequence).

The proteins encoded by these molecules are capable of associating with endogenous accessory proteins like DAP10 or DAP12. Alternatively, the nucleic acid molecules provided according to this aspect can be used as the CAR-encoding molecule in the combinations of nucleic acid molecules described herein.

According to a further aspect, vectors are provided comprising combinations of at least two isolated nucleic acid molecules, wherein at least one nucleic acid molecule encodes a chimeric antigen receptor (CAR), wherein the CAR comprises an antigen binding domain, a first transmembrane domain, and a signaling domain or costimulatory domain;

at least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule.

According to a further aspect, vectors are provided comprising nucleic acid molecules encoding a chimeric antigen receptor, wherein the CAR comprises an antigen binding domain, a transmembrane domain, and a signaling domain or costimulatory domain; and wherein the transmembrane domain is a NK receptor transmembrane domain and the antigen binding domain is not from the same NK receptor.

According to yet a further aspect, CAR complexes are provided herein that comprise at least one chimeric antigen receptor (CAR) molecule, wherein the CAR comprises an antigen binding domain, a first transmembrane domain, and a signaling domain or costimulatory domain; at least a second accessory protein comprising a second transmembrane domain and a signaling domain or costimulatory domain;

wherein the first transmembrane domain of the CAR molecule associates with the second transmembrane domain of the accessory protein; and wherein the CAR complex comprises both a signaling domain and a costimulatory domain, where one is present in the first and one in the second protein molecule.

According to a further aspect, mammalian cells are provided comprising the nucleic acid molecules, combination of nucleic acid molecules, vectors or CAR complexes as described herein.

Thus, according to particular embodiments, mammalian cells are provided that contain nucleic acid molecules encoding a chimeric antigen receptor, wherein the CAR comprises an antigen binding domain, a transmembrane domain, and a signaling domain or costimulatory domain; and wherein the transmembrane domain is a NK receptor transmembrane domain and the antigen binding domain is not from the same NK receptor.

According to alternative embodiments, the transmembrane domain in the vectors and cells can be a polyleucine transmembrane domain, as detailed for the nucleic acids described herein.

According to other particular embodiments, mammalian cells are provided that contain combinations of at least two isolated nucleic acid molecules, wherein at least one nucleic acid molecule encodes a chimeric antigen receptor (CAR), wherein the CAR comprises an antigen binding domain, a first transmembrane domain, and a signaling domain or costimulatory domain;

at least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule.

According to further particular embodiments, mammalian cells are provided that contain vectors comprising combinations of at least two isolated nucleic acid molecules, wherein at least one nucleic acid molecule encodes a chimeric antigen receptor (CAR), wherein the CAR comprises an antigen binding domain, a first transmembrane domain, and a signaling domain or costimulatory domain;

at least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule According to alternative particular embodiments, mammalian cells are provided that contain CAR complexes that comprise at least one chimeric antigen receptor (CAR) molecule, wherein the CAR comprises an antigen binding domain, a first transmembrane domain, and a signaling domain or costimulatory domain; at least a second accessory protein comprising a second transmembrane domain and a signaling domain or costimulatory domain;

wherein the first transmembrane domain of the CAR molecule associates with the second transmembrane domain of the accessory protein; and wherein the CAR complex comprises both a signaling domain and a costimulatory domain, where one is present in the first and one in the second protein molecule.

These mammalian cells typically are immune cells. According to specific embodiments, the cells are selected from a T cell, a NK cell, a NKT cell, a stem cell, a progenitor cell, and an iPSC cell. As explained in the definitions, stem cells or iPSC cells includes cells that are derived therefrom and (at least partly) differentiated towards being an immune cell.

According to a further aspect, methods are also provided of making such cells, comprising genetically modifying a mammalian cell with the nucleic acid molecule, combination of nucleic acid molecules, or one or more vectors as described herein. Genetic modification will typically be done by means of transduction, but other suitable methods may also be used. Further steps in the manufacturing of such cells may entail one or more steps of: obtaining the cells from a subject, purifying the desired cell population, differentiating the cell population (in case the immune cells are immature cells, such as stem cells, progenitor cells or iPSCs), activating the cell population, transducing the cell population with the vectors or combination of nucleic acid molecules as described herein, expanding the cell population, reformulating the cell population.

Also provided herein, according to a further aspect, are methods of treatment, using the modified immune cells described herein. These methods typically entail an administration step and a step of curing the disease or improving the disease symptoms.

Thus, according to particular embodiments, methods of treating cancer in a subject in need thereof are provided, comprising administering a modified immune cell to the subject, wherein the modified immune cell contains (and is able to express):

At least one isolated nucleic acid molecule encoding a chimeric antigen receptor (CAR), wherein the CAR comprises an antigen binding domain, a first transmembrane domain, and a signaling domain or costimulatory domain;

At least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule.

In these embodiments, the CAR will typically be directed against a tumor target (i.e. the antigen binding domain binds to a tumor antigen).

Likewise, according to alternative embodiments, methods of treating infection in a subject in need thereof are provided, comprising administering a modified immune cell to the subject, wherein the modified immune cell contains (and is able to express):

At least one isolated nucleic acid molecule encoding a chimeric antigen receptor (CAR), wherein the CAR comprises an antigen binding domain, a first transmembrane domain, and a signaling domain or costimulatory domain;

At least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule.

In these embodiments, the CAR will typically be directed against a target of the infectious organism (i.e. the antigen binding domain binds to an antigen present in an infectious organism, e.g. a viral antigen or a bacterial antigen).

Likewise, according to alternative embodiments, methods of treating inflammatory disease in a subject in need thereof are provided, comprising administering a modified immune cell to the subject, wherein the modified immune cell contains (and is able to express):

At least one isolated nucleic acid molecule encoding a chimeric antigen receptor (CAR), wherein the CAR comprises an antigen binding domain, a first transmembrane domain, and a signaling domain or costimulatory domain;

At least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule.

In these embodiments, the CAR will typically be directed against a target associated with the inflammatory disease (i.e. the antigen binding domain binds to an auto-antigen associated with the inflammatory disease).

The modified immune cells may be autologous immune cells (cells obtained from the patient) or allogeneic immune cells (cells obtained from another subject).

Optionally, the methods of treatment also contain one or more manufacturing steps prior to administration. Such manufacturing steps may contain for instance one or more of: obtaining the cells from a subject, purifying the desired cell population, differentiating the cell population (in case the immune cells are immature cells, such as stem cells, progenitor cells or iPSCs), activating the cell population, transducing the cell population with the vectors or combination of nucleic acid molecules as described herein, expanding the cell population, reformulating the cell population.

That methods of treatment are provided is equivalent as saying that the products described herein are provided for use as a medicament. Thus, nucleic acid molecules encoding a chimeric antigen receptor, wherein the CAR comprises an antigen binding domain, a transmembrane domain, and a signaling domain or costimulatory domain; and wherein the transmembrane domain is the NKG2D transmembrane domain; and the antigen binding domain is not from the NKG2D receptor are provided for use as a medicament. Also provided are combinations of at least two isolated nucleic acid molecules, wherein At least one nucleic acid molecule encodes a chimeric antigen receptor (CAR), wherein the CAR comprises an antigen binding domain, a first transmembrane domain, and a signaling domain or costimulatory domain;

At least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule for use as a medicament.

Further provided are vectors comprising combinations of at least two isolated nucleic acid molecules, wherein At least one nucleic acid molecule encodes a chimeric antigen receptor (CAR), wherein the CAR comprises an antigen binding domain, a first transmembrane domain, and a signaling domain or costimulatory domain;

At least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule, for use as a medicament.

Further provided are modified mammalian cells, particularly immune cells, containing (and able to express):

- At least one isolated nucleic acid molecule encoding a chimeric antigen receptor (CAR), wherein the CAR comprises an antigen binding domain, a first transmembrane domain, and a signaling domain or costimulatory domain;
- At least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule, for use as a medicament.

Most particularly, the compositions provided herein for use as a medicament are provided for use in the treatment of cancer. According to alternative embodiments, they are provided for use in the treatment of infectious disease. According to alternative embodiments, they are provided for use in the treatment of inflammatory disease.

DETAILED DESCRIPTION

Definitions

Figure 1:
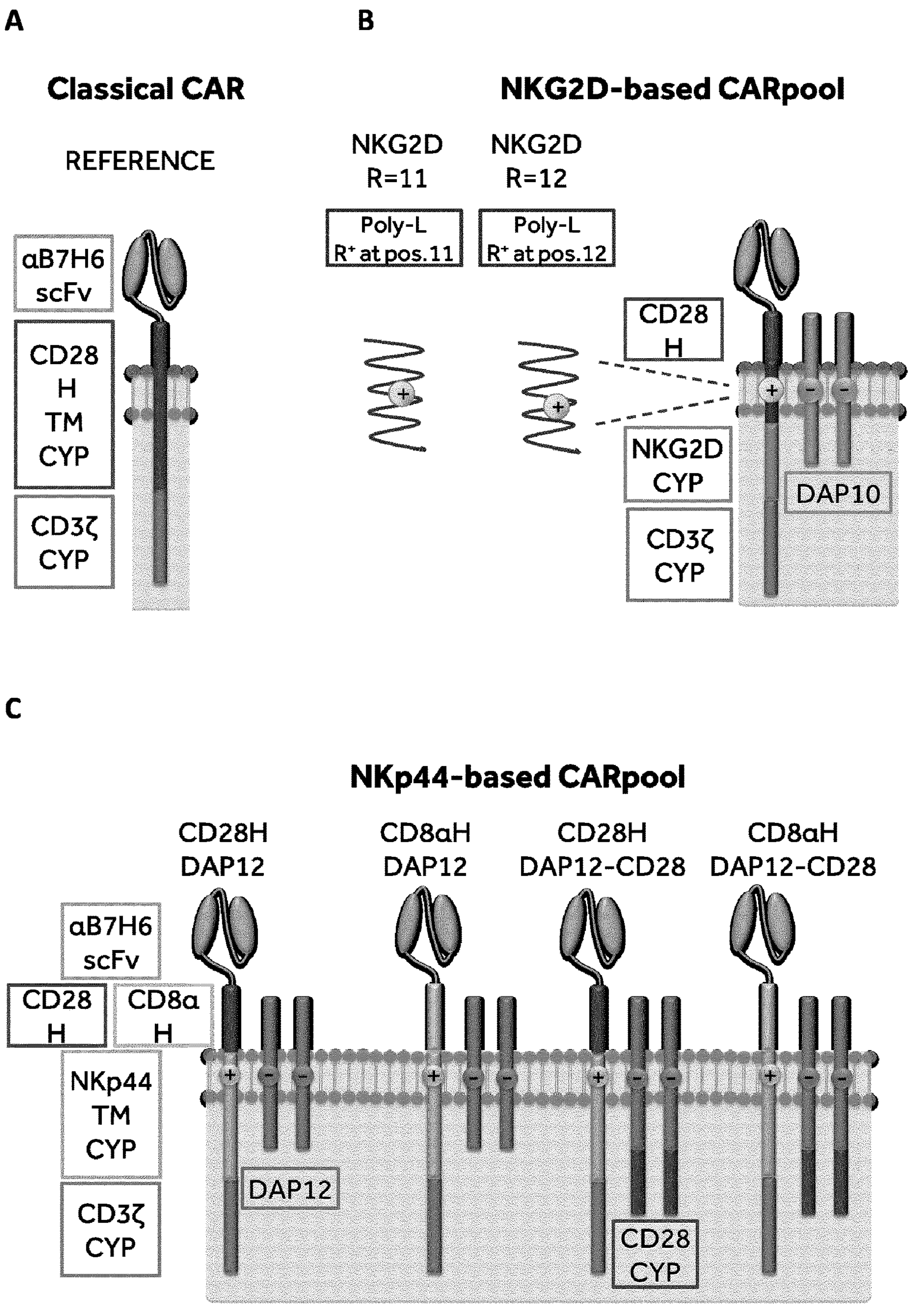
FIG. 1: CARpool design. A. Classical CAR architecture of a second generation CAR, with scFv binding domain, CD3ζ signaling domain and a costimulatory domain (here: CD28) in line on the same chain. B. CARpool design based on NKG2D transmembrane domain, or with NKG2D TM replaced by artificial transmembrane domain of polyleucines wherein a positively charged arginine residue has been introduced at indicated position. C. CARpool design with NKp44 transmembrane domain. Different hinge regions (CD8 or CD28) were used between the scFv and the transmembrane region as indicated. The costimulatory molecule DAP12 was used as such, or with an additional CD28 costimulatory domain fused to it.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. This particularly applies to the polypeptide chains, signaling domains, costimulatory domains, nucleic acid molecules and vectors described herein, where (unless otherwise indicated) 'a' or 'one' can mean 'one or more', and 'two' can mean 'two or more'.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention.

Unless specifically defined herein, all terms used herein have the same meaning as they would to one skilled in the art of the present invention. Practitioners are particularly directed to Green and Sambrook, Molecular Cloning: A Laboratory Manual, 4th ed., Cold Spring Harbor Laboratory Press, New York (2012); and Ausubel et al., Current Protocols in Molecular Biology (up to Supplement 114), John Wiley & Sons, New York (2016), for definitions and terms of the art. The definitions provided herein should not be construed to have a scope less than understood by a person of ordinary skill in the art.

The term "chimeric antigen receptor" or "CAR" as used herein refers to a chimeric receptor (i.e. composed of parts from different sources) that has at least a binding moiety with a specificity for an antigen (which can e.g. be derived from an antibody or a receptor), a transmembrane domain, and a moiety that can transmit a signal in an immune cell. The latter moiety may be a signaling domain (i.e. a domain derived from a receptor that signals by itself in immune cells, such as the T Cell Receptor (TCR) complex or the Fc receptor) or a costimulatory domain (i.e. a domain derived from a receptor that is required in addition to the TCR to obtain full activation, or the full spectrum of the signal in case of inhibitory costimulatory domains, of T cells). The costimulatory domain can be from an activating costimulatory receptor or from an inhibitory costimulatory receptor.

A "CAR complex" as used herein refers to a protein complex that contains at least one CAR chain and at least one accessory chain, wherein the accessory chain contains a transmembrane domain that interacts (associates) with the transmembrane domain of the CAR, and a signaling domain or costimulatory domain. Most typically, the CAR complexes described herein will only contain one antigen-binding domain (i.e., one chain with an antigen-binding domain, which can be dimerized, like in a typical CAR). According to specific embodiments, it is possible to have more than one binding domain (i.e. a bispecific or multispecific CAR), but CAR complexes with one binding domain are more typically envisaged.

A "transmembrane domain" or "TM domain" as used herein is any membrane-spanning protein domain. Most typically, it is derived from a transmembrane protein. However, it can also be artificially designed. Transmembrane domains used herein will typically associate with other transmembrane domains, through charged and non-charged interactions. CAR complexes typically contain at least two different chains, and thus at least two different transmembrane domains that associate with each other. Thus, artificial domains can be created (or naturally occurring TM domains can be selected) that associate with each other (e.g. because of complementary charges, hydrophobic interactions, or the like (or a combination of those)). Particularly envisaged transmembrane domains are domains that interact in a defined stoichiometry. Typical example of these are the NKG2D and DAP10 transmembrane domains or NKG2D and DAP12 transmembrane domains. Note that artificial domains with similar properties (e.g. hydrophobicity, charge distribution etc.) can be easily created to replace one or more of these domains. A particular example is a polyleucine chain, as this is a good hydrophobic region that is amenable to use in transmembrane domains. Charge can be incorporated in such polyleucine chain by incorporation of charged residues (preferably no more than three to retain the hydrophobic properties suitable for transmembrane domains, so particularly one or two charged residues are envisaged). Other examples of such domains that associate with each other are e.g. TCR alpha and beta TM domains on the one hand (which carry a strong positive and a positive charge respectively), and CD3 zeta, gamma, delta and epsilon TM domains (which carry a negative charge) on the other.

The term "NKG2D" as used herein refers to the protein that in humans is encoded by the KLRK1 gene (Gene ID: 22914). The "NKG2D transmembrane domain" is the membrane spanning domain of said protein. Typical sequences for this domain are PFFFCCFIAVAMGIRFIIMVA or PFFFCCFIAVAMGIRFIIMVT. The arginine residue gives this domain an overall net charge of +1.

The term "NKp44" as used herein refers to the protein that in humans is encoded by the NCR2 gene (Gene ID: 9436). The "NKp44 transmembrane domain" is the membrane spanning domain of said protein.

"DAP10" as used herein refers to the protein that in humans is encoded by the HSCT gene (GeneID: 10870). The "DAP10 transmembrane domain" is the membrane spanning domain of said protein. A typical sequence for this domain is LLAGLVAADAVASLLIVGAVF. The aspartate residue gives this domain an overall net charge of −1.

"DAP12" as used herein refers to the protein that in humans is encoded by the TYROBP gene (GeneID: 7305). The "DAP12 transmembrane domain" is the membrane spanning domain of said protein. A typical sequence for this domain is GVLAGIVMGDLVLTVLIALAV. The aspartate residue gives this domain an overall net charge of −1.

The term "immune cells" as used herein refers to cells that are part of the immune system (which can be either the adaptive or the innate immune system). Immune cells as used herein are typically immune cells that are manufactured for adoptive cell transfer (either autologous transfer or allogeneic transfer). Many different types of immune cells are used for adoptive therapy and thus are envisaged for use in the methods described herein. Examples of immune cells include, but are not limited to, T cells, NK cells, NKT cells, lymphocytes, dendritic cells, myeloid cells, stem cells, progenitor cells or iPSCs. The latter three are not immune cells as such, but can be used in adoptive cell transfer for immunotherapy (see e.g. Jiang et al., Cell Mol Immunol 2014; Themeli et al., Cell Stem Cell 2015). Typically, while the manufacturing starts with stem cells or iPSCs (or may even start with a dedifferentiation step from immune cells towards iPSCs), manufacturing will entail a step of differentiation to immune cells prior to administration. Stem cells, progenitor cells and iPSCs used in manufacturing of immune cells for adoptive transfer (i.e., stem cells, progenitor cells and iPSCs or their differentiated progeny that are transduced with a CAR as described herein) are considered as immune cells herein. According to particular embodiments, the stem cells envisaged in the methods do not involve a step of destruction of a human embryo.

Particularly envisaged immune cells include white blood cells (leukocytes), including lymphocytes, monocytes, macrophages and dendritic cells. Particularly envisaged lymphocytes include T cells, NK cells and B cells, most particularly envisaged are T cells. In the context of adoptive transfer, note that immune cells will typically be primary cells (i.e. cells isolated directly from human or animal tissue, and not or only briefly cultured), and not cell lines (i.e. cells that have been continually passaged over a long period of time and have acquired homogenous genotypic and phenotypic characteristics). According to specific embodiments, the immune cell is a primary cell. According to alternative specific embodiments, the immune cell is not a cell from a cell line.

The current invention is based on the finding that, whereas CARs typically function as a dimeric structure, this need not be the case. For instance, CARs based on the NKG2D receptor (such as those described in WO2006/036445) with a NKG2D transmembrane domain, rely on the signal of endogenous DAP10 molecules for full activation. The association of NKG2D with DAP10 is based on transmembrane interactions, primarily based on opposite charges and further stabilized by non-charged interactions. This association primarily based on opposite charges of transmembrane domains is well-documented in immune cells for e.g. the hexameric complex of NKG2D with DAP10 or DAP12 and for the octomeric TCR complex.

The present inventors showed that such signals can be modified: the endogenous DAP10 costimulatory domains can be replaced or supplemented with other costimulatory domains, as long as the transmembrane interaction remains intact (in this example: based on the transmembrane NKG2D-DAP10, NKG2D-DAP12, or NKp44-DAP12 interaction). This offers a number of advantages which combine the best of cis and trans CAR signaling: as the stoichiometry of the complex is well defined, the primary and costimulatory signal can be calibrated, just like in cis signaling. As the costimulatory domain is on a separate signaling chain, it is closer to the membrane (thus in a more natural configuration), which is known to be important. As the costimulatory domain is not on the same molecule as the signaling domain, the costimulatory domain in the CAR complex can be changed without the need for altering the CAR signaling chain (and thus without additional need of subcloning). Indeed, one can have a functional, first generation CAR construct (without costimulatory domains) and add chains with costimulatory domains to the complex according to what is needed (a 'mix and match' approach).

Particularly for complexes based on a NKG2D transmembrane domain, the complex is hexameric (with two NKG2D transmembrane chains and 4 DAP10 or DAP12 transmembrane chains), which means that the stoichiometry can be arranged in other ratios than 1:1 (e.g. 2:1 or 1:2), and that more than one different costimulatory domain can be used (e.g. in a 1:1:1 ratio). Note however that charged interactions are not limited to NKG2D transmembrane domains, and others can be used. Independent of the nature of the transmembrane domain, as the costimulatory domain is on a separate chain, transduction of chains with different costimulatory domains in a predefined ratio will allow association of a CAR complex that has the costimulatory domains in that ratio. Furthermore, in principle, using e.g. differentially activated promoters, it is possible to change the costimulatory domains in the complex. This can be particularly useful when a positive signal needs to be dialed down, and can be achieved by reducing/inhibiting expression of a chain with positive costimulatory signal and initiating/increasing expression of a chain with a negative costimulatory signal. Likewise, a positive costimulatory signal can be interchanged for a positive costimulatory signal of a different nature, as it is documented that costimulatory signals can initiate different signaling cascades.

An important advantage is that this modular nature obviates the need for further subcloning of specific CARs to change the costimulatory domain, as the CAR chain can now be supplemented with 'standard' accessory chains that contain a suitably associating transmembrane domain, and a particular signaling or costimulatory domain. For instance, a CAR complex with 4-1BB costimulatory domain can be altered in a CAR complex with CD28 costimulatory domain by replacing the accessory chain, without a need to alter the CAR chain.

In the scenarios described thus far, the CAR chain (i.e., the chain with an antigen-binding moiety and a first transmembrane domain) has the signaling moiety (the 'first signal') while the accessory chain comprises the complementary transmembrane domain and a costimulatory signal (the 'second signal'), so that the CAR chain can signal as such, but the signal is augmented when both are present. However, it is also possible to have a chain with an antigen-binding moiety and a costimulatory domain, while the signaling moiety is in the accessory chain.

Accordingly, it is an object of the invention to provide combinations of at least two isolated nucleic acid molecules, wherein

- At least one nucleic acid molecule encodes a chimeric antigen receptor (CAR), wherein the CAR comprises an antigen binding domain, a first transmembrane domain, and a signaling domain or costimulatory domain;
- At least a second nucleic acid molecule encodes an accessory protein comprising a second transmembrane domain and a signaling domain or costimulatory domain;
- wherein the first transmembrane domain of the CAR molecule associates with the second transmembrane domain of the accessory protein; and
- wherein the combination comprises both a signaling domain and a costimulatory domain, where one is encoded in the first and one in the second nucleic acid molecule.

According to particular embodiments, combinations of two isolated nucleic acid molecules are provided, wherein

- the first nucleic acid molecule encodes a chimeric antigen receptor (CAR), wherein the CAR comprises an antigen binding domain, a first transmembrane domain, and a signaling domain or costimulatory domain;
- the second nucleic acid molecule encodes an accessory protein comprising a second transmembrane domain and a signaling domain or costimulatory domain;
- wherein the first transmembrane domain of the CAR associates with the second transmembrane domain of the accessory protein; and wherein the combination comprises both a signaling domain and a costimulatory domain, where one is encoded in the first and one in the second nucleic acid molecule.

When these combinations of nucleic acid molecules are expressed, the CAR protein and accessory protein will associate with each other through their transmembrane domains, forming a functional CAR complex. This means that, when the antigen binding domain binds to its cognate antigen, both the signaling domain and costimulatory domain are activated (i.e. transmit a signal).

It is to be understood that the combinations can contain more than two nucleic acid molecules. This will for instance be the case in complexes where more than one accessory protein is present, e.g. to incorporate more than one signaling or costimulatory domains on different protein chains.

Isolated means that they are discreet molecules, but they can be provided on one plasmid or vector. Typically, if that is the case, they will be separated in other ways, e.g. by having separate promoters, or by being separated by an IRES sequence or the like.

The isolated nucleic acid molecules will typically be engineered nucleic acid molecules. According to particular embodiments, the accessory protein is also a chimeric protein (and thus not identical to an endogenously occurring protein). Note however that this is not a prerequisite: in case of e.g. DAP10 and DAP12, the transmembrane domain and costimulatory domain can be derived from one protein.

According to particularly envisaged embodiments, the signaling domain will be present in the CAR chain and the costimulatory domain in the accessory chain. This way, the CAR chain can already function as a first generation CAR and is not dependent on other molecules for signaling. However, according to alternative embodiments, the CAR chain carries a costimulatory domain and the accessory protein has the signaling domain.

According to particular embodiments, the signaling domain is selected from the group consisting of a CD3 zeta chain, a Fc epsilon RI gamma chain, a CD3 epsilon chain or a ZAP70 chain. According to particularly preferred embodiments, the signaling domain is a CD3 zeta chain. According to specific embodiments, the complex does not contain any chain derived from the Fc epsilon RI receptor. According to alternative specific embodiments, the complex does not contain any transmembrane domain derived from a FC epsilon RI receptor.

Note that, although the CAR complex has been described as allowing the combination of chains with a single signaling domain and chains with a single costimulatory domain, further combinations can be envisaged as well. For instance, the chains can carry more than one signaling domain (either identical or different), more than one costimulatory domain (identical or different), or a combination of both one or more signaling domains and costimulatory domains. They can also incorporate extra parts of signaling domains (e.g. contain an extra Immunoreceptor tyrosine-based activation (ITAM) or inhibition (ITIM) motif). In those instances where mainly a stronger signal is desired, it is also possible to use only chains containing signaling domains (i.e., without costimulatory domains)—the nature of the complex ensures that this way, more signaling domains will be present than in a classical CAR design.

According to particular embodiments, the costimulatory domain is selected from CD28, 4-1BB, OX40, ICOS, DAP10, DAP12, CD27, CD2, GITR, TLA, CD30 and HVEM. According to further particular embodiments, the costimulatory domain is selected from CD28, 4-1BB, OX40, ICOS, DAP10, DAP12, CD27, and CD2. Even more particularly, the costimulatory domain is selected from CD28, 4-1BB, OX40, ICOS, DAP10, and DAP12.

The antigen-binding domain of the CAR chain can be any suitable antigen-binding domain as present in a CAR. Typically, the domain will be an scFV, the ligand binding domain of a receptor, an antibody or a VHH. Typically, the antigen-binding domain will bind to an antigen or target that is associated with a disease. E.g. a target that is associated with inflammation, or a target that is present on an infectious organism (e.g. a virus or bacterium). Most typically, the CAR will be directed against a tumor target. By way of non-limiting examples, the CAR can be directed e.g. against B7H6, BCMA, CAIX, CD7, CD16, CD19, CD20, CD22, CD27 (TNFRSF7), CD30 (TNFRSF8), CD33, CD38, CD52, CD56, CD70 (TNFSF7), CD123 (IL3R alpha), CD133, CEA, CLD18 (claudin 18, splice variant 2), CLL1, cMET, CS1, EGFR, EGFRvIII, EpCAM, ErbB123, FAP (fibroblast activation protein), folate receptor alpha, GD2, GPC3, HER1, HER2 (also Neu, ErbB2 or CD340), IL-1A, IL13R alpha 2 (CD213A2), kappa light chain, L1-CAM, LeY, mesothelin, MUC-1, MUC16, NKG2D, NKp30, NKp44, NKp46, NY-ESO1, PD-1, PDL-1, PIGF, PSCA, PSMA, ROR-1, or VEGFR2.

The nature of the transmembrane domains is such that the transmembrane domains of the CAR chain will associate with the transmembrane domains of the accessory protein chain, when both are suitably expressed in a mammalian cell. Such association is mediated by protein-protein interactions. These interactions can be because of charge complementarity (ionic interactions), electrostatic interactions, hydrogen bonds, van der Waals interactions, hydrophobic interactions, solvent-dependent interactions, backbone-dependent interactions, alpha-helical interactions, beta-sheet interactions and the like. Typically, transmembrane domains are quite hydrophobic, so these interactions tend to be more important. An important mechanism by which transmembrane protein chains associate is charge complementarity, i.e. one TM domain will carry a positive charge, while the other will carry a negative charge. Typically, the positive charge is due to the presence of positively charged amino acids such as R or K (or sometimes H). The negative charge on the other hand is due to the presence of negatively charged amino acids such as D or E. Thus, when selecting or designing suitable TM domains, this feature can be taken into account. As most charged residues are quite polar and not hydrophobic (nor amenable to incorporation in secondary protein structures such as beta sheets), the number of charged residues in a TM domain will typically be limited. "Association" as used herein in the context of TM domains means that two different transmembrane domains will interact with each other, and bind each other to the extent that the chains they are part of are brought into proximity. As a result of said proximity (that is stabilized by the association of the complementary transmembrane domains), the complex can form a functional signaling unit.

According to specific embodiments, the first and second transmembrane domains have an opposite charge and the association is through ionic interactions. According to particularly envisaged embodiments, the positively charged transmembrane domain is a NKp44 transmembrane domain, and the negatively charged transmembrane domain is a suitable transmembrane domain interacting with the NKp44 TM domain. According to particularly envisaged embodiments, the positively charged transmembrane domain is a NKG2D transmembrane domain, and the negatively charged transmembrane domain is a suitable transmembrane domain interacting with the NKG2D TM domain. According to further particularly envisaged embodiments, the positively charged transmembrane domain is a NKp44 transmembrane domain, and the negatively charged transmembrane domain is selected from a DAP10 and a DAP12 transmembrane domain. Most particularly, it is a DAP12 domain. According to further particularly envisaged embodiments, the positively charged transmembrane domain is a NKG2D transmembrane domain, and the negatively charged transmembrane domain is selected from a DAP10 and a DAP12 transmembrane domain. Most particularly, it is a DAP10 domain. The NKG2D or NKp44 TM domain can be present both in the CAR chain and in the accessory protein chain, but the resulting stoichiometry of the complex will be different: the natural NKG2D complex is a hexameric complex with two NKG2D chains and 4 DAP10 or DAP12 chains. Thus, by changing which TM domain is in the CAR chain and which in the accessory protein chain, the stoichiometry of the complex can change.

According to alternative embodiments, the negatively charged transmembrane domain is a DAP12 domain, and the positively charged transmembrane domain is a domain selected from a NKG2D TM domain, a KIR TIM domain, a Ly49 TM domain, a NKG2C TM domain, and a NKp44 TM domain.

Considering the suitability of the NKG2D TM domain in the CAR complexes described herein, a particularly useful nucleic acid molecule provided herein is one encoding a chimeric antigen receptor, wherein the CAR comprises an antigen binding domain, a transmembrane domain, and a signaling domain or costimulatory domain; and wherein the transmembrane domain is the NKG2D or NKp44 transmembrane domain. According to specific embodiments, the antigen binding domain is not from the NKG2D or NKp44 receptor. According to specific embodiments, the molecule contains a signaling domain and a costimulatory domain. According to alternative embodiments, the molecule contains either a signaling domain or a costimulatory domain. An advantage of the molecule containing a signaling domain is that the CAR can already signal without the complex being fully formed, so even when expression is not efficient, a signal can be generated. Also, by placing the one or more nucleic acid molecules encoding the accessory chains under control of an inducible promoter, the complex can be assembled at a suitable time or place (temporal, spatial or spatiotemporal control) to modify or strengthen the signal. An advantage of the molecule containing a costimulatory domain but not a signaling domain is that the CAR complex will only signal when fully assembled. Although no external dimerizers are needed (in contrast to conditionally active heterodimeric CARs) and assembly of the complex occurs upon expression of the individual chains, this can act both as a safety check, or can be used for spatial, temporal or spatiotemporal control of CAR expression (by e.g. placing one or more of the nucleic acid molecules encoding the CAR complex chains under control of an inducible promoter).

This particular nucleic acid molecule can be used in the combinations mentioned herein. It can also be used with endogenous proteins, for instance, in cells expressing endogenous DAP10 or DAP12, expression of such nucleic acid molecule will result in a CAR complex with endogenous DAP10 or DAP12 as an accessory chain. However, it is particularly envisaged that the accessory chain is also encoded by an engineered nucleic acid molecule. The signaling domain and costimulatory domain are as described herein.

According to particular embodiments, also provided herein are one or more vectors comprising the combinations of nucleic acid molecules described herein, or the particular, NKG2D-TM domain encoding nucleic acid molecule described herein. The combinations can be provided on one or more plasmids or vectors: the former reduces the number of molecules to be transduced in a cell, the latter may be envisaged if more than one accessory chain is present in the complex, or if more control is needed on expression levels. Typically, the vectors will be viral vectors (e.g. lentiviral vectors or retroviral vectors), but other suitable vectors for modifying immune cells may also be used.

Likewise, according to a further aspect, CAR complexes are provided herein that comprise at least one chimeric antigen receptor (CAR) molecule, wherein the CAR comprises an antigen binding domain, a first transmembrane domain, and a signaling domain or costimulatory domain; at least a second accessory protein comprising a second transmembrane domain and a signaling domain or costimulatory domain;

wherein the first transmembrane domain of the CAR molecule associates with the second transmembrane domain of the accessory protein; and wherein the CAR complex comprises both a signaling domain and a costimulatory domain, where one is present in the first and one in the second protein molecule.

Also provided are mammalian cells comprising the nucleic acid molecules, combination of nucleic acid molecules, vectors or CAR complexes as described herein. These mammalian cells typically are immune cells. According to specific embodiments, the cells are selected from a T cell, a NK cell, a NKT cell, a stem cell, a progenitor cell, and an iPSC cell. As explained in the definitions, stem cells or iPSC cells includes cells that are derived therefrom and (at least partly) differentiated towards being an immune cell.

Methods are also provided of making such cells, comprising genetically modifying a mammalian cell with the nucleic acid molecule, combination of nucleic acid molecules, or one or more vectors as described herein. Genetic modification will typically be done by means of transduction, but other suitable methods may also be used.

Also provided herein are methods of treatment, using the modified immune cells described herein. These methods typically entail an administration step and a step of curing the disease or improving the disease symptoms.

Thus, methods of treating cancer in a subject in need thereof are provided, comprising administering a modified immune cell to the subject, wherein the modified immune cell contains (and is able to express):

- At least one isolated nucleic acid molecule encoding a chimeric antigen receptor (CAR), wherein the CAR comprises an antigen binding domain, a first transmembrane domain, and a signaling domain or costimulatory domain;
- At least a second nucleic acid molecule encodes an accessory protein comprising a second transmembrane domain and a signaling domain or costimulatory domain;
- wherein the first transmembrane domain of the CAR molecule associates with the second transmembrane domain of the accessory protein; and
- wherein the combination comprises both a signaling domain and a costimulatory domain, where one is encoded in the first and one in the second nucleic acid molecule.

In these embodiments, the CAR will typically be directed against a tumor target (i.e. the antigen binding domain binds to a tumor antigen).

Likewise, methods of treating infection in a subject in need thereof are provided, comprising administering a modified immune cell to the subject, wherein the modified immune cell contains (and is able to express):

- At least one isolated nucleic acid molecule encoding a chimeric antigen receptor (CAR), wherein the CAR comprises an antigen binding domain, a first transmembrane domain, and a signaling domain or costimulatory domain;

At least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule.

In these embodiments, the CAR will typically be directed against a target of the infectious organism (i.e. the antigen binding domain binds to an antigen present in an infectious organism, e.g. a viral antigen or a bacterial antigen).

Likewise, methods of treating inflammatory disease in a subject in need thereof are provided, comprising administering a modified immune cell to the subject, wherein the modified immune cell contains (and is able to express):

- At least one isolated nucleic acid molecule encoding a chimeric antigen receptor (CAR), wherein the CAR comprises an antigen binding domain, a first transmembrane domain, and a signaling domain or costimulatory domain;

At least a second nucleic acid molecule encodes an accessory protein comprising a second transmembrane domain and a signaling domain or costimulatory domain;

- wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule.

In these embodiments, the CAR will typically be directed against a target associated with the inflammatory disease (i.e. the antigen binding domain binds to an auto-antigen associated with the inflammatory disease).

The modified immune cells may be autologous immune cells (cells obtained from the patient) or allogeneic immune cells (cells obtained from another subject).

Optionally, the methods of treatment also contain one or more manufacturing steps prior to administration. Such manufacturing steps may contain for instance one or more of: obtaining the cells from a subject, purifying the desired cell population, differentiating the cell population (in case the immune cells are immature cells, such as stem cells, progenitor cells or iPSCs), activating the cell population, transducing the cell population with the vectors or combination of nucleic acid molecules as described herein, expanding the cell population, reformulating the cell population.

That methods of treatment are provided is equivalent as saying that the products described herein are provided for use as a medicament. Thus, nucleic acid molecules encoding a chimeric antigen receptor, wherein the CAR comprises an antigen binding domain, a transmembrane domain, and a signaling domain or costimulatory domain; and wherein the transmembrane domain is a NK receptor transmembrane domain; and the antigen binding domain is not from the same NK receptor are provided for use as a medicament. Also provided are combinations of at least two isolated nucleic acid molecules, wherein

- At least one nucleic acid molecule encodes a chimeric antigen receptor (CAR), wherein the CAR comprises an antigen binding domain, a first transmembrane domain, and a signaling domain or costimulatory domain;

At least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule for use as a medicament.

Further provided are vectors comprising combinations of at least two isolated nucleic acid molecules, wherein At least one nucleic acid molecule encodes a chimeric antigen receptor (CAR), wherein the CAR comprises an antigen binding domain, a first transmembrane domain, and a signaling domain or costimulatory domain;

At least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule, for use as a medicament.

Further provided are modified mammalian cells, particularly immune cells, containing (and able to express):

At least one isolated nucleic acid molecule encoding a chimeric antigen receptor (CAR), wherein the CAR comprises an antigen binding domain, a first transmembrane domain, and a signaling domain or costimulatory domain;

At least a second nucleic acid molecule encodes an accessory protein comprising a second transmembrane domain and a signaling domain or costimulatory domain;

wherein the first transmembrane domain of the CAR molecule associates with the second transmembrane domain of the accessory protein; and wherein the combination comprises both a signaling domain and a costimulatory domain, where one is encoded in the first and one in the second nucleic acid molecule, for use as a medicament.

Most particularly, the compositions provided herein for use as a medicament are provided for use in the treatment of cancer. According to alternative embodiments, they are provided for use in the treatment of infectious disease. According to alternative embodiments, they are provided for use in the treatment of inflammatory disease.

It is to be understood that although particular embodiments, specific configurations as well as materials and/or molecules, have been discussed herein for cells and methods according to present invention, various changes or modifications in form and detail may be made without departing from the scope and spirit of this invention. The following examples are provided to better illustrate particular embodiments, and they should not be considered limiting the application. The application is limited only by the claims.

EXAMPLES

CARs are modular receptors that consist of a target binding moiety fused to structural domains including an extracellular spacer, a transmembrane region and intracellular signaling domains. These signaling regions typically comprise a tandem alignment of co-stimulatory (e.g. CD28, CD137) and activating (CD3) domains that upon target binding initiate activation of T cell effector functions. This linear configuration displays a rigid spatial orientation and ratio of co-stimulation to activation domains. To address this, we have developed a novel mix-and-match approach (CARpool) where the costimulatory signal is provided in trans on accessory proteins that associate with the antigen binding chain via transmembrane-mediated interactions, potentially driving the ability to tailor T cell responses upon CAR activation.

Example 1. Generation of a CAR Complex with CARpool Design

By exploiting the ability of NK activating receptors to assemble as multi-subunit complexes via interactions between membrane-embedded opposite charges, several CD3ζ-containing CAR chains were designed using the transmembrane (TM) and cytoplasmic (CYP) domains of NKG2D or NKp44, able to associate with DAP10 and DAP12 respectively [9-11]. NKG2D TM was replaced by a polyleucine sequence of the same length as the NKG2D TM domain with the positively charged residue at position 11 or 12, allowing its interaction with DAP10 (which is based on opposite charges). Each CAR included a B7H6 specific scFv. The CAR- and accessory protein-encoding sequences were co-expressed with a selection marker using 2A self-cleaving sites. These constructs were compared to a classical second-generation CAR construct employing CD28 as costimulatory domain [12] (FIG. 1).

Example 2. Characterization of Cells Expressing CARpool Complexes

Cell Surface Expression Varied Between CARpool Designs

Figure 2:
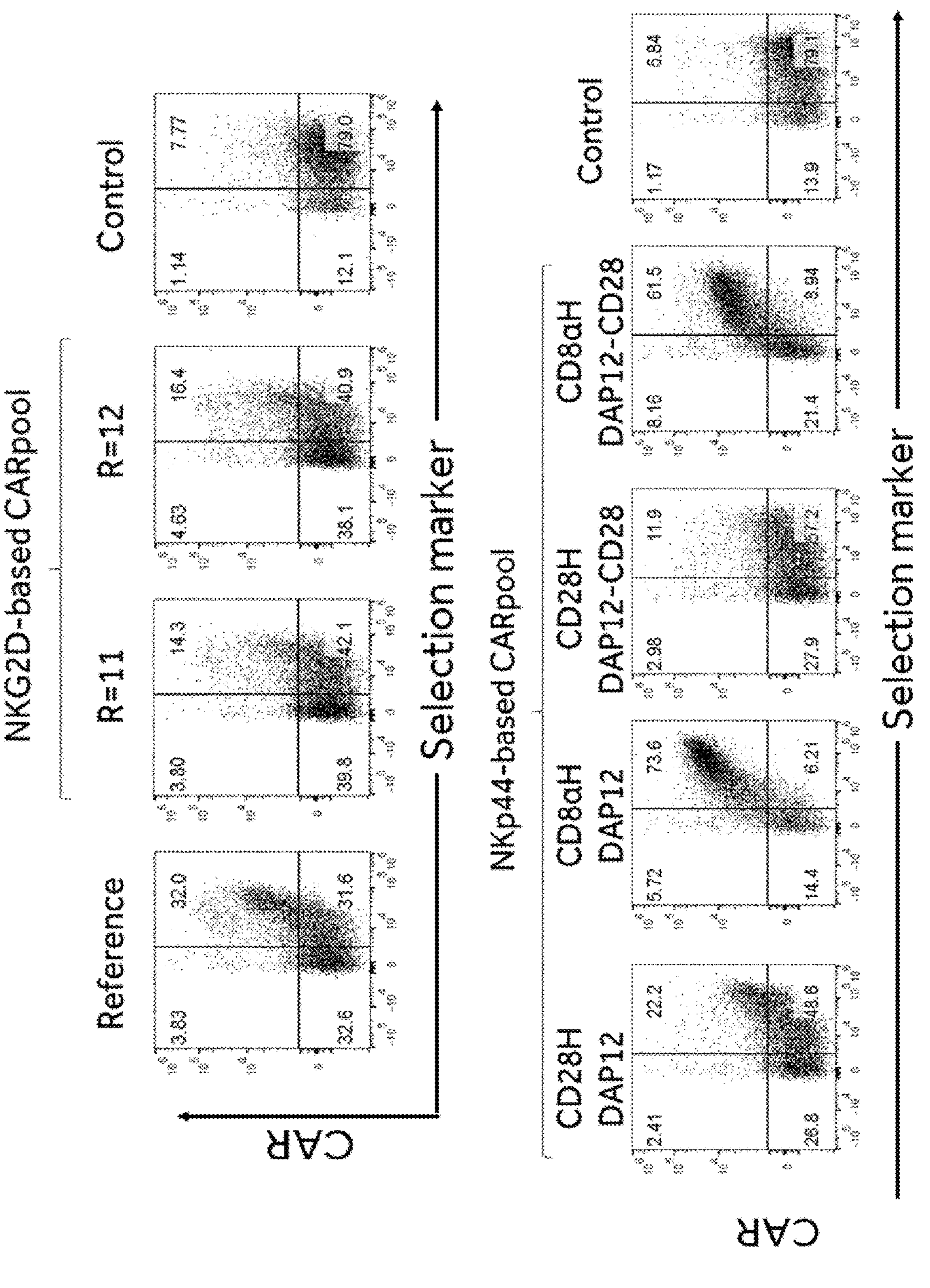
FIG. 2: Expression of different CARpool constructs on human T cells.

CAR and selection marker expressions were assessed by flow cytometry (FIG. 2). CARpool complexes based on the NKG2D-design (i.e. with NKG2D cytoplasmic domain and NKG2D or polyleucine transmembrane domain) showed reduced expression levels compared to the reference CAR. NKp44-based CARpool constructs containing the CD8a hinge showed expression levels largely superior to the respective CD28 hinge-containing CARs. Addition of CD28 costimulatory domain to DAP12 significantly decreased CAR cell surface expression.

Cellular Phenotype was not Altered by CARpool Expression

Figure 3:
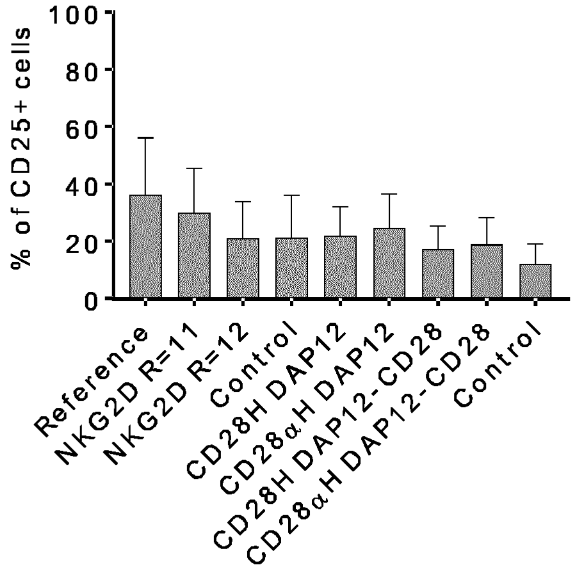
FIG. 3: Phenotype of CARpool T cells A: by CD25 expression. B: by T cell subtype
Figure 3:
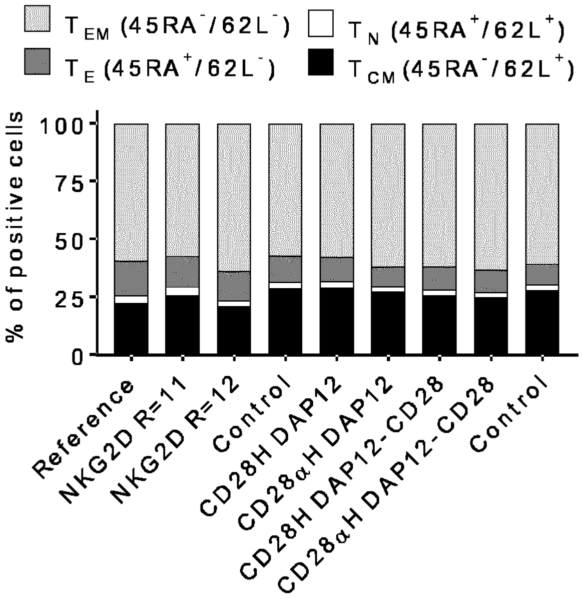

CARpool T cells exhibited a trend to express less CD25 activation marker compared to the reference CAR (FIG. 3A). Analysis of the differentiation status based on the expression of CD62L and CD45RA delineating 4 functional subsets (Naïve, Central memory, Effector memory and Effector T cells) revealed that these cells were mainly composed of memory cells (FIG. 3B). No major difference in activation and memory phenotype between CARpool and reference CAR T cells could be observed.

Example 3: CARpool T Cells Showed Potent In Vitro Anti-Tumor Activity

Figure 4:
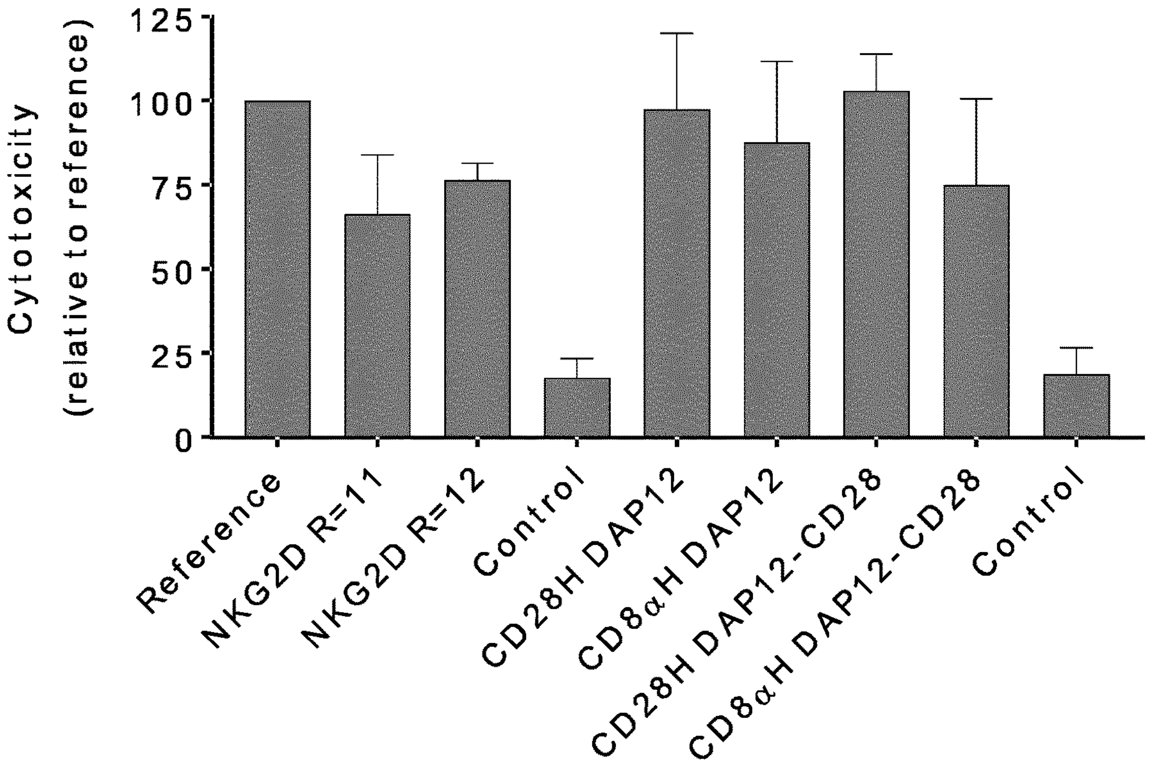
FIG. 4: antitumor activity of CARpool T cells

All CARpool T cells showed potent cytotoxicity against the cervix carcinoma cell line HeLa (FIG. 4). NKG2D-based CARpool T cells (R=11 and R=12) showed similar cytolytic activities. NKp44-based CARpool T cells incorporating the CD28 hinge were more potent compared to those with the CD8a hinge and were equivalent to the reference CAR.

Supplementation of DAP12 with CD28 costimulatory domain did not improve cell functionality. Similar results were obtained for cytotoxicity against K562 leukemia cells (data not shown).

Figure 5:
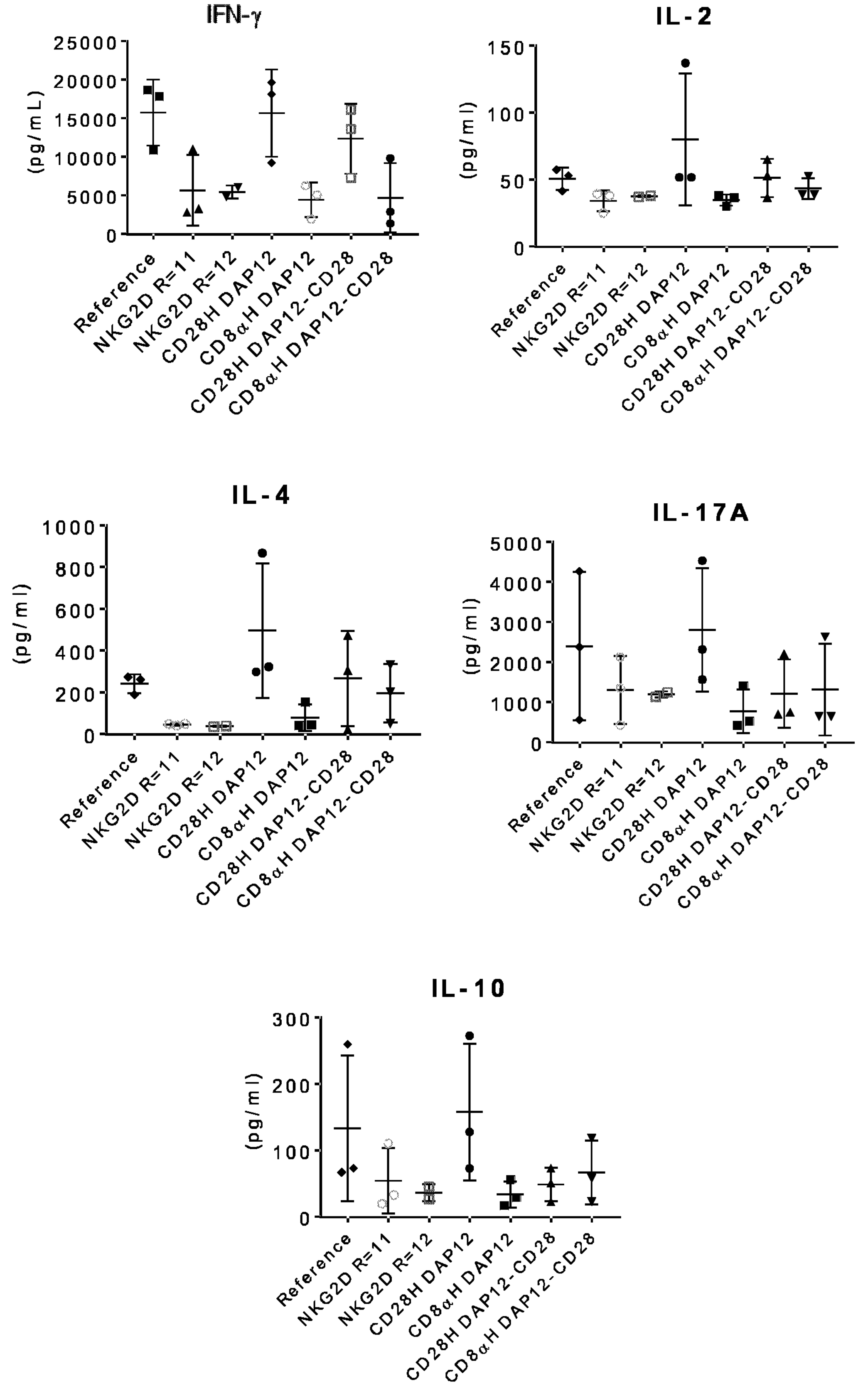
FIG. 5: cytokine secretion of CARpool T cells

To interrogate whether target cell engagement by the distinct CARpool T cells drives distinct cytokine release profiles, supernatants of coculture with Hela cells were analyzed using a multiplex assay (FIG. 5). T cells bearing the NKp44 CARpool with the CD28 hinge co-expressing DAP12 showed the highest levels of secretion for all types of cytokines equivalent to the reference CAR T cells. Here again, fusion of DAP12 to CD28 cytoplasmic domain did not alter the pattern and levels of cytokine secretion.

These studies provide proof-of-concept for novel modulatory CAR complexes with improved flexibility compared to a classical CAR design. Future directions include:

In vivo evaluation of CARpool anti-tumor activity
Incorporation of different scFv targeting other antigens
Interchange of costimulatory domains (both in the accessory chain and interchanged with CD3ζ in the main signaling chain)

REFERENCES

1. Fesnak A D, June C H, Levine B L (2016) Engineered T cells: the promise and challenges of cancer immunotherapy. Nat Rev Cancer. 16: 566-81. doi: 10.1038/nrc.2016.97
2. Brenner M K (2017) Next Steps in the CAR Journey of a Thousand Miles. Mol Ther. 25: 2226-7. doi: 10.1016/j.ymthe.2017.09.013
3. Davila M L, Brentjens R J (2016) CD19-Targeted CAR T cells as novel cancer immunotherapy for relapsed or refractory B-cell acute lymphoblastic leukemia. Clin Adv Hematol Oncol. 14: 802-8.
4. Kochenderfer J N, Somerville R P T, Lu T et al. (2017) Long-Duration Complete Remissions of Diffuse Large B Cell Lymphoma after Anti-CD19 Chimeric Antigen Receptor T Cell Therapy. Mol Ther. 25: 2245-53. doi: 10.1016/j.ymthe.2017.07.004
5. Park J H, Geyer M B, Brentjens R J (2016) CD19-targeted CAR T-cell therapeutics for hematologic malignancies: interpreting clinical outcomes to date. Blood. 127: 3312-20. doi: 10.1182/blood-2016-02-629063
6. Rossig C (2017) CAR T cell immunotherapy in hematology and beyond. Clin Immunol. doi: 10.1016/j.clim.2017.09.016
7. Turtle C J, Hay K A, Hanafi L A et al. (2017) Durable Molecular Remissions in Chronic Lymphocytic Leukemia Treated With CD19-Specific Chimeric Antigen Receptor-Modified T Cells After Failure of Ibrutinib. J Clin Oncol. 35: 3010-20. doi: 10.1200/JCO.2017.72.8519
8. Rezvani K, Rouce R, Liu E, Shpall E (2017) Engineering Natural Killer Cells for Cancer Immunotherapy. Mol Ther. 25: 1769-81. doi: 10.1016/j.ymthe.2017.06.012
9. Garrity D et al. PNAS 2005; 102:7641-7646
10. Feng J et al. PLOS Biology 2006; 4:0768-0779
11. Lanier L Immunol Reviews 2009; 227:150-160
12. Wu M et al. Gene Therapy 2015; 22:675-684

The invention claimed is:

1. A combination of nucleic acid molecules which when co-expressed result in a functional chimeric receptor, which comprises:

(a) a first nucleic acid molecule which comprises a nucleic acid encoding an antigen binding domain, a hinge region, a nucleic acid encoding the NKG2D transmembrane (TM) domain or a nucleic acid encoding a polylysine of the same length as NKG2D TM which has been modified to comprise an arginine at position 11 or 12, wherein sequence numbering corresponds to that of the native NKG2D transmembrane domain, a nucleic acid encoding the cytoplasmic (CYP) domain of NKG2D, and a CD3zeta signaling domain and (b) a second nucleic acid molecule which encodes at least the TM region of DAP10 and further comprises the endogenous DAP10 signaling domain or a CD28 costimulatory domain;

wherein the TM domain encoded by the first nucleic acid associates with the TM domain of DAP10 encoded by the second nucleic acid; thereby resulting in a functional CAR, and wherein the antigen binding domain encoded by the first nucleic acid binds to B7H6.

2. The combination of nucleic acid molecules of claim 1 embodiment (i), wherein the hinge region comprises a CD28 or CD8a hinge region.

3. A combination of nucleic acid molecules which comprises:

(a) a first nucleic acid molecule which comprises a nucleic acid encoding an antigen binding domain, a CD28 or CD8a hinge, a nucleic acid encoding the NKp44™, a nucleic acid encoding the cytoplasmic (CYP) domain of NK44, and a CD3zeta signaling domain; and (b) a second nucleic acid molecule which encodes at least the TM region of DAP12 and further comprises the endogenous DAP12 signaling domain or a CD28 costimulatory domain;

wherein the TM domain encoded by the first nucleic acid of (a) associates with the TM domain of the DAP12 accessory protein encoded by the second nucleic acid of (b), thereby resulting in a functional CAR, and wherein the antigen binding domain encoded by the first nucleic acid binds to B7H6.

4. The combination of nucleic acid molecules of claim 3, wherein the hinge region comprises a CD28 or CD8a hinge region.

5. The combination of nucleic acid molecules of claim 1, wherein the antigen binding domain is an scFv.

6. The combination of nucleic acid molecules of claim 3, wherein the antigen binding domain is an scFv.

7. The combination of nucleic acid molecules of claim 1, which result in a functional CAR when the first and second nucleic acids of (i) are co-expressed in an immune cell which expresses a selection marker comprising 2A self-cleaving sites.

8. The combination of nucleic acid molecules of claim 3, which result in a functional CAR when the first and second nucleic acids are co-expressed in an immune cell which expresses a selection marker comprising 2A self-cleaving sites.

9. A cell which expresses a combination of nucleic acid molecules of according to claim 1.

10. The cell of claim 8, which is selected from a T cell, a NK cell, a NKT cell, a stem cell, a progenitor cell, and an iPSC cell.

11. A cell which expresses a combination of nucleic acid molecules of according to claim 3.

12. The cell of claim 11, which is selected from a T cell, a NK cell, a NKT cell, a stem cell, a progenitor cell, and an iPSC cell.

* * * * *